United States Patent [19]

Coleman

[11] Patent Number: 5,124,480

[45] Date of Patent: Jun. 23, 1992

[54] PEROXYGEN BLEACH ACTIVATORS AND BLEACHING COMPOSITIONS

[75] Inventor: James P. Coleman, Maryland Heights, Mo.

[73] Assignee: Monsanto Company, St. Louis, Mo.

[21] Appl. No.: 418,595

[22] Filed: Oct. 10, 1989

[51] Int. Cl.[5] .......................... C07C 67/02; C09K 3/00
[52] U.S. Cl. ............................... 562/874; 252/186.38; 558/262
[58] Field of Search .................... 562/874; 252/186.38

[56] References Cited

U.S. PATENT DOCUMENTS

| | | | |
|---|---|---|---|
| 98,106 | 6/1883 | Gray et al. | |
| 147,191 | 12/1884 | Hagemann et al. | |
| 738,671 | 6/1880 | Efimova et al. | |
| 3,257,382 | 6/1966 | Bell | 562/874 |
| 3,272,750 | 9/1966 | Chase et al. | 252/99 |
| 3,412,179 | 11/1968 | Kleiner | 562/874 |
| 3,419,603 | 12/1968 | Lipowski et al. | 260/500.5 |
| 3,691,234 | 9/1972 | Kiefer et al. | 562/874 |
| 3,707,502 | 12/1972 | Rawllness | 252/99 |
| 3,725,289 | 4/1973 | Mouret | 252/95 |
| 3,779,931 | 12/1973 | Fries et al. | 252/99 |
| 3,825,585 | 7/1974 | Chappelow et al. | 260/500.5 |
| 3,925,234 | 12/1975 | Hachmann et al. | 252/186 |
| 4,422,950 | 12/1983 | Kemper | 252/186.38 |
| 4,957,647 | 9/1990 | Zielske | 252/186.38 |

OTHER PUBLICATIONS

The Hydroxamic Acids, by Harry L. Yale, Shell Development Company, Sep. 21, 1943.

*Primary Examiner*—Richard D. Lovering
*Assistant Examiner*—Joseph D. Anthony
*Attorney, Agent, or Firm*—R. C. Loyer

[57] ABSTRACT

The present invention relates to N,O-diacyl,N-acyl hydroxylamines and their use as bleach activators in conjunction with oxygen-releasing compounds.

7 Claims, No Drawings

PEROXYGEN BLEACH ACTIVATORS AND BLEACHING COMPOSITIONS

This invention relates to novel compounds and compositions useful in peroxygen bleaching. More particularly, this invention relates to novel N,O-diacyl,N-alkyl hydroxylamine compounds that aid in providing effective and efficient peroxygen bleaching of articles over a wide range of temperatures and conditions.

This invention also relates to detergent compositions containing materials which provide efficient bleach compounds in situ by means of a combination of N,O-diacyl,N-alkyl hydroxylamine activator compounds and other compounds yielding hydrogen peroxide in solution.

BACKGROUND OF THE INVENTION

Peroxygen bleaches have long been known to be effective in removing stains and/or soils from textiles and the like. Detergent compositions containing an oxygen-releasing compound, for example an inorganic persalt, such as an alkali metal perborate or percarbonate or peroxides such as urea peroxide have been disclosed as useful for bleaching and sanitizing purposes. Such bleaches, however, are highly dependent on temperature for efficiency. For example, temperatures in the range of about 95° C. to about 100° C. are satisfactory for such bleaches while temperatures lower than about 75° C. have been shown to decrease the efficiency of the bleach to an unsatisfactory level.

In recent times textiles have been made which are best laundered in low temperature wash water. Such temperatures are in the range of unsatisfactory performance for the above-mentioned bleaches. Further, concern for energy conservation has created a need for laundry detergents, and other materials such as bleaches, such that all textiles can be laundered at lower temperatures at which previously known bleaches are unsatisfactory.

Previous attempts to overcome the disadvantages noted above have resulted in various teachings and prior patents relating to detergent formulations containing oxygen-releasing compounds such as persalts and peroxides with the goal of providing more effective bleaching and sanitizing activity in temperatures as low as 50° C., usually between 50° C. and about 75° C. Typical examples of such attempts are described in U.S. Pat. No. 3,256,198 to Matzner issued Jun. 14, 1966. Matzner discloses generically alkyl and aryl carbonates wherein the aryl may be substituted, for example, by halo, nitro and sulfo groups. The alkyl groups or radicals may contain from about 1 to 20 carbon atoms. However, only dialkyl or diaryl symmetrical carbonates in a limited class of compounds are demonstrated as being useful.

In another attempt to solve the problem of bleaching efficiency in relatively low temperature laundering processes, sodium p-sulfophenyl alkyl carbonates were disclosed to be useful in U.S. Pat. No. 3,272,750 to Chase, issued Sep. 13, 1966. However, the relatively low molecular weight alkyl and phenyl carbonates disclosed therein do not demonstrate bleaching efficiency adequate for present needs.

Since the need for energy conservation has become more acute in recent years, there have been more recent attempts to increase the efficiency of bleaches in low temperature wash water. In most instances, a peroxide-ester bleaching composition has been taught to be useful and as having higher efficiency than the previous combination of low molecular weight carbonates with persalts. Examples of this art are found in U.S. Pat. No. 4,539,130 to Thompson, et al. Acyloxybenzene sulfonates are disclosed as efficient peroxygen bleach activator compounds useful in detergent compositions at relatively low wash water temperatures. A review of the prior art of bleach activator compounds is disclosed in this patent which is hereby incorporated by reference. Other examples of recent attempts to establish greater efficiency in bleach activator compounds useful in laundering at relatively low temperatures are represented by European Patent application 0 147 191 to Hegemann et al published Jul. 3, 1985, and European Patent application 0 098 108 to Garner-Gray published Jan. 11, 1984. These European patent applications contain a large list of peroxygen bleach activator compounds including a few carbonates in common with the U.S. patents to Matzner and Chase referred to above.

SUMMARY OF THE INVENTION

It is an object of the present invention to provide particularly effective peroxygen surface bleaching compounds.

The present invention provides peroxygen bleach activator compounds represented by the formula:

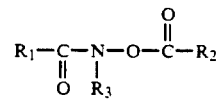

wherein $R_1$ is selected from the group consisting of hydrogen and straight or branched chain alkyl groups having from 1 to about 6 carbon atoms, $R_2$ is straight or branched chain alkyl or alkoxy groups having from about 1 to about 12 carbon atoms and $R_3$ is a straight or branched chain alkyl group having from about 1 to about 9 carbon atoms.

Compositions are also provided comprising a mixture of (1) an oxygen-releasing compound such as an inorganic persalt, and (2) a bleach activator N,O-diacyl,N-alkylhydroxylamines of this invention.

Yet another aspect of the present invention provides methods for bleaching articles which comprises contacting the articles with a composition comprising a mixture of (1) an oxygen-releasing compound selected from inorganic persalts, and (2) a bleach activator, N,O-diacyl,N-alkylhydroxylamines of this invention.

The compounds of the invention are employed in combination with a peroxygen bleaching compound capable of yielding hydrogen peroxide in an aqueous solution to provide particularly effective peroxygen bleaching over a wide range of temperatures and conditions. The novel compositions of the invention, while possessing excellent bleaching efficiency at low temperatures, also can be manufactured at relatively less expense than other peroxygen bleach activator compounds designed to operate at relatively low laundering temperatures.

DETAILED DESCRIPTION

Preferably the alkyl moieties $R_1$ and $R_2$ of the acyl groups in the above structural formula will contain from 1 to about 9 carbon atoms while of $R_1$ is $C_1$ and $R_2$ is a linear $C_9$ derivative. Preferably alkyl group $R_3$ in the above structural formula will contain from about 1 to about 3 carbons atoms while $C_1$ derivatives have been found to be most preferred. Compositions of this invention may comprise mixtures of compounds described by the above structural formula. The bleach activator derivatives need only to be slightly soluble in water.

The groups $R_1$, $R_2$ and $R_3$ of the above formula may contain substitutents which are non-interfering with the bleach activator function of the compounds. Examples of non-interfering substituents are halides such as chlorine, bromine or iodine, or substitutents such as nitro, cyano, sulfo, alkoxy, carboxymethyl, and the like.

In the above formula the organic radicals $R_1$, $R_2$ and $R_3$ may represent any of the wide variety of straight or branched chain alkyl groups. Examples of unsubstituted branched chain alkyl groups or radicals include isohexyl, isononyl, isodecyl, 2-ethylhexyl and the like. The branched chain radicals preferably contain from about 1 to about 9 carbon atoms in the group. Similarly, the straight chain groups likewise preferably contain from about 1 to about 9 carbon atoms.

The compounds of this invention can be prepared by a two-step procedure in which the N-alkylhydroxylamine is first acylated to give a hydroxamic acid. Acylating agents may be carboxylic acid chlorides, anhydrides, esters or alkyl chloroformates. The hydroxamic acid may then be acylated on the oxygen using such acid chloride or anhydride or formate to give the N,O-diacyl,N-alkyl hydroxylamine.

The preparation may take place in accordance with the following equations:

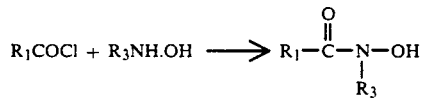

Particularly preferred compounds of this invention are those wherein the acyl portions of the N,O-diacyl,N-alkyl hydroxylamine is linear having an alkyl moiety containing from about 1 to about 9 carbon atoms and the alkyl portion of the N,O-diacyl,N-alkyl hydroxylamine is linear and having from about 1 to about 3 carbon atoms.

The N,O-diacyl,N-alkyl hydroxylamines of this invention can be prepared by known methods such as the reaction of N-alkyl hydroxamic acids with carboxylic acid chlorides.

Suitable N,O-diacyl,N-alkyl hydroxylamines as herein defined may be mixed, preferable in the solid state, with a wide variety of inorganic oxygen-releasing compounds to provide the compositions of this invention. Examples of inorganic oxygen-releasing compounds include inorganic peroxides, such as alkaline earth metal peroxides, for example, calcium, magnesium, zinc and barium peroxides. Other suitable inorganic peroxides include alkali metal carbonate peroxides, such as sodium percarbonate and alkali metal pyrophosphate peroxides, such as sodium pyrophosphate peroxide. Particularly suitable inorganic oxygen-releasing compounds include inorganic persalts, such as metal and ammonium persulfates and perborates. Of these persalts, water-soluble alkali metal (for example, sodium, potassium, etc.) persulfates and perborates are preferred, and alkali metal perborates, especially sodium and potassium perborates, are particularly preferred.

The ingredients of the compositions of this invention may be present in various proportions depending upon whether the composition is to be used as a bleaching composition, a washing composition, or both. However, in most instances, such compositions contain either an organic or an inorganic oxygen-releasing compound and from about 0.1 to about 6 moles, per mole of the oxygen-releasing compound, of the useful hydroxylamines.

Compositions of this invention can be used primarily as a bleach, for instance, for addition to alkaline textile bleaching baths or wash liquors. Such compositions may contain any proportion of N,O-diacyl,N-alkyl hydroxylamines of this invention and persalts, these components being preferably present in the ratio of 1 to 10 moles of peroxygen producing compound per mole of N,O-diacyl,N-alkyl hydroxylamines, preferably from about 2 to about 4 moles per mole of hydroxylamine. Thus, by way of example a composition may contain 10% of persalt having 10–15% available oxygen and about 2% to about 25% of the N,O-diacyl,N-alkyl hydroxylamines of this invention. Using persalt having 16% available oxygen, the composition may contain 7% of the persalt and 6.5% of the N,O-diacyl,N-alkyl hydroxylamines.

When a detergent is present in compositions according to this invention improvements in bleaching can be obtained in normal washing concentrations. Thus, for example, using a detergent composition according to the invention at a concentration of about 0.1% to about 0.2% in aqueous solution, improvements may be obtained if amounts as little as about 1% of persalt and about 1% of the hydroxylamine derivatives of this invention, by weight of the composition, are present. In such compositions, however, the amount of persalt taken should provide at least about 0.1% available oxygen based on the composition. Generally detergent compositions will contain from about 5% to about 15% by weight of organic detergent. The mixed N,O-diacyl,N-alkyl hydroxylamine/persalt content may be as high as about 15% by weight provided that these components are taken in ratios of about 1:1 to 1:10 and preferably 1:2 to 1:4 molecules of N,O-diacyl,N-alkyl hydroxylamine and persalt in detergent compositions will generally be in the range of from about 2% to about 30% of the N,O-diacyl,N-alkyl hydroxylamine and from about 1% to about 15% of persalt by weight of the composition.

Best results in bleaching according to the invention are obtained under conditions of effective agitation such as exist, for instance, in a washing machine. Compositions according to this invention should preferably contain one or more alkaline substances in amounts such that similar compositions not containing the N,O-diacyl,N-alkyl hydroxylamine would give a pH value within the range of about 8–11 when dissolved at the desired bleaching concentration. Most common detergent compositions contain alkaline material sufficient for this purpose. Suitable alkaline materials are, for example, alkali metal carbonates, phosphates (including orthophosphates and water-soluble condensed phosphates such as tripolyphosphates and pyrophosphates) and silicates. When the compositions of this invention are applied to bleaching or wash water, alkali sufficient to give an initial pH of from about 9 to about 11 is preferably present in the bleaching or wash water.

Compositions according to the present invention may contain any of the conventional adjuncts present in detergent compositions. These include optional components as are described in U.S. Pat. No. 4,539,130 referred to above and incorporated herein by reference.

The above disclosure generally describes the invention. A more complete understanding can be obtained by reference to the following specific examples which are provided herein for purposes of illustration only and are not to limit the scope of the invention.

EXAMPLE 1

Preparation of N-methyl,O-nonanoyl, acetohydroxamic Acid.

In a 2-liter, 3-necked flask equipped with a mechanical stirrer and condenser, N-methylhydroxylamine hydrochloride (61.6 g, 0.7 mole) was dissolved in methylene chloride (700 ml). Triethylamine (77.77 g, 0.77 mole) was added, then acetyl chloride (54.95 g, 0.7 mole) was added dropwise, while cooling the flask in a water bath to maintain temperature at about 25° C. When addition was complete the mixture was stirred for 1.5 hours at room temperature. A sample analyzed by UV-visible spectroscopy of the iron hydroxamate complex indicated an 88% yield of hydroxamic acid.

Pyridine (55.3 g, 0.7 mole) was added to the solution, followed by dropwise addition of n-nonanoyl chloride (116.6 g, 0.7 mole). The solution was left at room temperature for two days then washed with water, dilute HCl, dilute sodium carbonate solution in water and dried over anhydrous sodium carbonate. The solution was then filtered and stripped on a rotovap to leave a clear yellow liquid (133.60 g). The product was distilled under vacuum (3 mm Hg) to give 93.26 g (b.p. 151°-155° C.) of N-methyl,O-nonanoyl,acetohydroxamic acid.

EXAMPLE 2

Preparation of N-isopropyl,O-nonanoyl acetohydroxamic acid

A

In a screw capped jar with a magnetic stirring bar N-isopropylhydroxylamine hydrochloride (23.1 g, 97%, 0.2 moles) was dissolved in water (150 ml) and sodium hydroxide (8.0 g, 0.2 mole) added. Acetic anhydride (22.44 g, 0.22 mole) was added slowly, then sufficient water to bring the total volume up to 200 ml. The jar was than sealed and placed in an oil bath at 78° C. After 2.75 hours analysis of a sample by UV-visible spectroscopy of the iron-hydroxamate complex showed a 96.5% yield of hydroxamic acid. The heating period is necessary to rearrange the initially formed O-acylated hydroxylamine into the hydroxamic acid.

B

To 20 ml of the above solution was added sodium hydroxide (0.8 g, 0.02 mole) to neutralize residual acetic acid. The aqueous solution was then extracted with 5×20 ml portions of methylene chloride which were combined, dried over anhydrous magnesium sulfate and filtered.

To the filtrate was added pyridine (1.6 g, 0.02 mole) and n-nonanoyl chloride (3.53 g, 0.02 mole) at room temperature. The solution was stirred for 2 days at room temperature then washed with water, dilute HCl, water and sodium carbonate solution before being dried over anhydrous sodium carbonate, filtered and stripped to leave a pale yellow oil (3.22 g) which analyzed as 83.5% N-isopropyl,O-nonanoyl acetohydroxamic acid.

EXAMPLE 3

Preparation of N-isopropyl,O-nonanoyl formohydraxamic acid.

N-isopropyl hydroxylamine hydrochloride (2.31 g, 97%, 0.02 mole), triethylamine (2.02 g, 0.02 mole) and methyl formate (1.50 g, 0.025 mole) were made up to 20 ml with methylene chloride and sealed in a screw cap jar with a stirring bar. The solution was heated to 64° C. for 20 hours at which time a sample was taken and analyzed by UV-visible spectroscopy, after addition to ferric nitrate solution, and showed a 75% yield of hydroxamic acid.

The mixture was stripped to dryness to remove methanol, redissolved in methylene chloride (20 ml) and treated with pyridine (1.6 g) and n-nonanoyl chloride (3.5 g, 0.02 mole). After one hour the solution was washed with water, dilute HCl and saturated sodium carbonate solution, dried over anhydrous sodium carbonate and stripped to leave 3.52 g of clear yellow liquid which was analyzed by GC as 74% pure N-isopropyl, O-nonanoyl formohydroxamic acid.

EXAMPLE 4

Preparation of Dodecanedioyl O,O-bis (N-methyl,N-acetyl hydroxylamine).

N-methylhydroxylamine hydrochloride (8.80 g, 0.1 mole) and triethylamine (11.11 g, 0.11 mole) were added to methylene chloride (100 ml) in a 200 ml 3-necked flask. Acetic anhydride (10.2 g, 0.1 mole) was added dropwise and the mixture stirred overnight.

Pyridine (7.90 g, 0.1 mole) was then added, followed by the dropwise addition of dodecane-1,12-dioyl chloride (13.35 g, 0.05 mole). The mixture was stirred for four hours then washed sequentially with dilute HCl and a dilute sodium carbonate solution, then dried over anhydrous magnesium sulfate. After filtration and stripping, a light yellow liquid (9.40 g) was obtained which slowly solidified to a waxy solid. NMR and mass spectrometry confirmed the desired structure, namely, 1,12-dodecane dioyl O,O-bis(N-methyl,N-acetyl hydroxylamine).

By similar procedures other compounds of this invention can be prepared.

EXAMPLE 5

In all of the examples below a commercial detergent sold under the trademark Tide ® containing 8.4% by weight phosphorus was employed as a control at a use level of 1.5 g/L of wash solution. A secondary control was employed whereby the above-mentioned commercial detergent was combined with sodium perborate (tetrahydrate) at a use level of 0.15 g/L of wash solution. Various bleach activator compounds were added to the detergent/perborate composition in the amounts shown in Table I.

All of the examples below were conducted at the same wash conditions of 100° F. and with water having a hardness level of 150 ppm (calcium carbonate). In each test a set of these swatches measuring 4 inches by 6 inches was evenly stained. After staining, the light reflectance value (Rd) was measured using the Gardner Xl-23 Tristimulator Colorimeter (Gardner Laboratory, Inc., Bethesda, Md.).

A Terg-o-tometer was employed to test the bleaching performance of the bleach activator compounds. In each test three stained swatches were placed in a cylindrical container with 1 L of water. Two minutes was allowed for the detergent to dissolve in the water.

In bleach activator tests sufficient sodium perborate was added to the wash water to provide 16 ppm available oxygen. The amount of bleach activator employed was based on 4 ppm available oxygen from the organic peracid generated, that is, a 4 to 1 mole ratio of perborate to bleach activator compound. The washing operation covered a period of 10 minutes after which the laundered swatches were rinsed with clear water and dried. Light reflectance measurements of each swatch were made and averaged. The difference ($\Delta Rd$) of these readings for each type of stain are reported in Table I. The term "AN" in the following Table I refers to appearance number. The higher number in appearance number is desired. In Table I samples A-D, employing compounds of this invention are compared to samples E-I of the prior art, including sample H containing only sodium perborate and sample I containing detergent only. The data indicates that samples A-D provided greatly improved stain removal over the prior art hydroxylamines and greatly superior performance over controls H and I.

Samples J-M, employing compounds of this invention are to be compared with samples N and O which contained perborate only and detergent only respectively. There is again shown greatly improved results in bleach action by employing the bleach activator of this invention.

TABLE I

| Sample | Chemical Name | Activity % | M.W. | gm/L | Clay/Cotton 100° F. $\Delta Rd$ | Clay/Cotton 150 ppm AN | Coffee/PE-Cot 100° F. $\Delta RD$ | Coffee/PE-Cot 150 ppm AN | Coca-Milk-Sugar/Cotton 100° F. $\Delta Rd$ | Coca-Milk-Sugar/Cotton 150 ppm AN | Clay/Cotton 76° F. $\Delta Rd$ | Clay/Cotton 150 ppm AN | Average of 1, 2, and 3 100° F. $\Delta Rd$ | Average of 1, 2, and 3 150 ppm AN |
|---|---|---|---|---|---|---|---|---|---|---|---|---|---|---|
| A | N,O-diacetyl Methylhydroxylamine | 98 | 131 | .1310 .044 | 29.6 25.8 | 33.5 28.1 | 9.9 12.0 | 15.0 13.6 | 7.5 4.1 | 7.4 5.8 | — — | — — | 15.7 14.0 | 18.6 15.1 |
| B | N-acetyl, O-nonanoyl, N-methyl hydroxylamine | 77 | 229 | .2743 .091 | 28.6 28.7 | 33.1 32.4 | 13.4 14.2 | 16.5 18.4 | 8.3 7.4 | 7.5 8.5 | — 24.2 | — 27.0 | 16.7 16.8 | 19.0 29.8 |
| C | N-nonanoyl, O-acetyl, N-methyl hydroxylamine | 75 | 229 | .2787 .093 | 23.3 25.0 | 19.9 22.0 | 12.0 11.9 | 15.1 15.2 | 4.3 6.1 | 4.1 7.2 | — — | — — | 13.2 14.3 | 13.1 14.8 |
| D | N—O-diacetyl, N-isopropyl hydroxylamine | 100 | 159 | .1550 .052 | 25.1 25.9 | 27.8 28.3 | 10.3 11.1 | 14.0 14.4 | — — | — — | — — | — — | — — | — — |
| E | Triacetyl hydroxylamine | | 159 | .1590 .053 | 27.1 24.1 | 30.1 26.1 | 9.7 11.3 | 13.4 12.8 | 7.8 4.6 | 6.5 5.5 | — — | — — | 14.9 13.3 | 16.7 13.3 |
| F | N,O-diacetyl hydroxylamine | 95 | 117 | .1170 .040 | 26.0 25.3 | 30.2 28.2 | 11.0 10.0 | 13.8 13.6 | 4.3 3.7 | 4.3 5.2 | — — | — — | 13.8 13.0 | 16.1 15.7 |
| G | N,acetyl, O-nonanoyl hydroxylamine | 25 | 215 | .2150 .072 | 24.7 24.6 | 27.7 27.1 | 10.6 11.6 | 13.6 13.1 | 3.8 5.7 | 5.6 7.2 | — — | — — | 13.0 14.0 | 15.6 15.8 |
| H | No Activator, Sodium Perborate alone (10% A.O.) | | 154 | .1500 | 24.9 | 27.5 | 10.3 | 13.1 | 3.9 | 5.0 | — | — | 13.0 | 15.2 |
| I | Tide (8.4% P) | | — | | 22.9 | 25.7 | 10.0 | 13.0 | 3.9 | 6.2 | 19.5 | 21.9 | 12.3 | 15.0 |
| J | N-acetyl, O-nonanoyl N-isopropyl hydroxylamine | 85 | 257 | .2942 .0981 | 26.79 27.11 | 29.39 29.85 | | | | | | | | |
| K | N-methyl, O-nonanoyl formohydroxamic acid | 75 | 215 | .2786 .0929 | 28.58 28.21 | 29.34 30.84 | | | | | | | | |
| L | Dodecanedioyl, O,O-bis(N-Methyl, N-acetyl hydroxylamine | | 374 | .3642 .1214 | 29.39 27.10 | 32.23 29.67 | | | | | | | | |
| M | N-isopropyl, O-Nonanoyl formohydroxamic acid | 75 | 243 | .3146 .1049 | 28.60 28.29 | 27.80 29.80 | | | | | | | | |
| N | Sodium perborate | | | .1500 | 24.33 | 26.65 | | | | | | | | |
| O | Tide | | | 1.5 | 22.44 | 25.13 | | | | | | | | |

EXAMPLE 6

In further tests as described in Example 2 above, other compounds of this invention were employed as bleach activators with detergent and sodium perbocate. Control samples employing only perborate and only detergent were also tested. The results of these tests are reported in Table II below.

TABLE II

| Sample | Chemical Name | Activity % | M.W. | gm/L | Clay/Cotton 100° F. $\Delta Rd$ | Clay/Cotton 150 ppm AN | PE-Cot 100° F. $\Delta RD$ | PE-Cot 150 ppm AN |
|---|---|---|---|---|---|---|---|---|
| P | N-acetyl-O-nonanoyl-N-methyl hydroxylamine | 100 | | .1190 .0595 .0298 | 30.15 28.71 27.20 | 34.46 32.46 30.34 | 17.71 19.59 15.62 | 9.87 11.17 9.92 |
| Q | O-2-ethylhexyl-Carobnyl-N-isopropylaceto hydroxamic acid | 58 | | .1530 | 26.16 | 28.78 | 14.64 | 11.25 |
| R | Sodium perborate | | | .1600 | 24.76 | 26.82 | 11.87 | 9.35 |
| S | Tide | | | 1.5 | 22.80 | 24.71 | 12.43 | 8.47 |

I claim:
1. A compound represented by the formula:

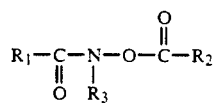

Wherein $R_1$ is selected from the group consisting of hydrogen and straight or branched chain alkyl groups having from 1 to about 6 carbon atoms, $R_2$ is selected from the group consisting straight or branched chain alkyl or alkoxy groups having from about 1 to about 12 carbon atoms and $R_3$ is selected from the group consisting of straight or branched chain alkyl groups having from about 1 to about 3 carbon atoms.

2. The compound of claim 1 wherein $R_1$ and $R_2$ are straight chain alkyl groups and $R_3$ is methyl.

3. The compound of claim 2 wherein $R_1$ and $R_2$ are methyl groups.

4. The compound of claim 2 wherein $R_1$ is methyl and $R_2$ is octyl.

5. The compound of claim 2 wherein $R_1$ is n-octyl and $R_2$ is methyl.

6. The compound of claim 1 wherein $R_1$ and $R_2$ are straight chain alkyl groups and $R_3$ is isopropyl.

7. The compound of claim 6 wherein $R_1$ and $R_2$ are methyl.

* * * * *